(12) United States Patent
Böhm et al.

(10) Patent No.: US 7,826,651 B2
(45) Date of Patent: Nov. 2, 2010

(54) METHOD FOR OPERATING AN X-RAY DIAGNOSTIC APPARATUS FOR DETERMINING QUALITY VALUES

(75) Inventors: Stefan Böhm, Oberasbach (DE); Peter Durlak, Erlangen (DE); Volker Heer, Gundelsheim (DE); Martin Kolarjk, Nürnberg (DE)

(73) Assignee: Siemens Aktiengesellschaft, Munich (DE)

( * ) Notice: Subject to any disclaimer, the term of this patent is extended or adjusted under 35 U.S.C. 154(b) by 60 days.

(21) Appl. No.: 12/401,295

(22) Filed: Mar. 10, 2009

(65) Prior Publication Data

US 2009/0169088 A1 Jul. 2, 2009

Related U.S. Application Data

(62) Division of application No. 11/293,444, filed on Dec. 2, 2005, now Pat. No. 7,539,336.

(30) Foreign Application Priority Data

Dec. 13, 2004 (DE) ....................... 10 2004 060 127

(51) Int. Cl.
*G06K 9/00* (2006.01)
(52) U.S. Cl. .............................. 382/130; 128/922; 378/4
(58) Field of Classification Search ................. 382/100, 382/128, 130, 131, 132; 128/922; 378/4–27, 378/37, 38, 46, 63, 90, 92, 98.4, 98.6, 98.9
See application file for complete search history.

(56) References Cited

U.S. PATENT DOCUMENTS

| 3,069,654 | A | | 12/1962 | Hough | |
| 4,707,786 | A | | 11/1987 | Dehner | |
| 4,761,819 | A | * | 8/1988 | Denison et al. | ............. 382/261 |
| 5,081,357 | A | | 1/1992 | Agano | |
| 5,181,234 | A | * | 1/1993 | Smith | ........................... 378/87 |
| 5,436,829 | A | | 7/1995 | Hartley | |
| 5,594,807 | A | * | 1/1997 | Liu | ............................. 382/128 |
| 5,651,042 | A | * | 7/1997 | Dewaele | ....................... 378/62 |
| 5,850,465 | A | * | 12/1998 | Shimura et al. | .............. 382/132 |
| 2003/0198403 | A1 | * | 10/2003 | Ottesen | ....................... 382/280 |

OTHER PUBLICATIONS

James T. Dobbins III; "Handbook of Medical Imaging"; 2000; pp. 1-5 and 163-222; vol. 1. Physics and Psychophysics; Chapter 3—Image Quality Metrics for Digital Systems; SPIE, Bellingham, Washington.
William K. Pratt; "Digital Image Processing"; 1978; pp. 522-525 and 548-549; John Wiley & Sons; New York, NY.

* cited by examiner

*Primary Examiner*—Anand Bhatnagar

(57) ABSTRACT

A method for checking an x-ray diagnostic apparatus is provided. Fluoroscopic series of x-ray images of a technical phantom are digitally acquired and stored. Difference between a dynamic image and a background image is calculated. A measuring field is predicted. Priori information about the shape of a clinically relevant object is determined. Hough transformation on a gray value image corresponding to the difference is applied. Contrast of the object from the Hough-transformed gray value image is determined. A square of the determined contrast is calculated. A noise variance is calculated by determining a sum of a noise variance of a homogenous image region and a variance of the background image. A contrast-to-noise ratio of the determined contrast and the calculated noise variance is determined. A square of the contrast-to-noise ratio is dynamically averaged. A Clinical Relevant Fluoroscopy Performance index for the x-ray diagnostic apparatus is determined.

1 Claim, 4 Drawing Sheets

METHOD FOR OPERATING AN X-RAY DIAGNOSTIC APPARATUS FOR DETERMINING QUALITY VALUES

CROSS REFERENCE TO RELATED APPLICATIONS

This is a divisional application of U.S. patent application Ser. No. 11/293,444, filed Dec. 2, 2005, now U.S. Pat. No. 7,539,336 which claims priority of German application No. 10 2004 060 127.5, filed Dec. 13, 2004. Both applications are incorporated by reference herein in their entirety.

FIELD OF INVENTION

The invention relates to an angiographic x-ray diagnostic apparatus comprising an x-ray radiator with an x-ray tube, a patient positioning table with a radiation-transparent positioning plate and mattress, an x-ray detector as well as an imaging system and an image processing unit. The invention further relates to measuring methods for checking an x-ray diagnostic apparatus as well as measuring methods for checking clinically relevant objects by means of a standardized x-ray diagnostic apparatus.

BACKGROUND OF INVENTION

Fluoroscopic or angiographic x-ray diagnostic apparatuses of this kind are commonly used nowadays in the therapy of certain vascular diseases whereby the patient has an angiographic implant such as a stent inserted at the diseased location in the vessel in an intervention. The key to fast and precise positioning of the stent lies in excellent x-ray visibility of items such as catheters and guide wires as well as implants such as stents, it frequently being the case that the visibility of the structures varies from manufacturer to manufacturer. This is attributable on the one hand to the x-ray diagnostic apparatus and on the other to the size of the objects.

To gauge the image quality of x-ray diagnostic apparatuses, various measuring methods using technical phantoms such as DQE for flat-panel detectors (Detective Quantum Efficiency, effective quantum absorption), resolution tests and edge are well known. These methods are described e.g. in the "Handbook of Medical Imaging", Volume 1, Physics and Psychophysics, Chapter 3, Image Quality Metrics for Digital Systems, 2000. However, they only take account of isolated technical issues and not the clinically relevant behavior of the overall system.

SUMMARY OF INVENTION

An object of the present invention is to implement a device of the abovementioned type in such a way as to allow image quality assurance, taking into account the clinical relevance of the overall system of angiographic x-ray diagnostic apparatuses, so that different x-ray equipments as well as clinically relevant objects can be compared with one another. Another object of the invention is to implement methods of the abovementioned type as a means of comparing different x-ray equipments as well as clinically relevant objects with one another.

According to the invention, this object is achieved for an x-ray diagnostic apparatus by providing a measuring device to which the output signals of the x-ray detector are fed and which has a first device for determining a value determining the reproduction quality of clinically relevant objects, a second device for calculating local noise variances in a homogeneous image region of different x-ray images and a device for taking the ratio of the output values of the two devices.

The measuring device can be incorporated in the x-ray diagnostic apparatus as hardware or software. However, it can also be implemented on a separate computer, such as a personal computer with appropriate software.

It has been found advantageous for the first device to have a prediction stage for predicting the position of a clinically relevant object.

According to the invention, the first device can in this case have a lookup table (LUT) with a priori knowledge concerning the shape of the clinically relevant object.

Advantageously the first device can have a subtraction stage for taking the difference between a current image extracted from a series of continuous images and a background image.

According to the invention the output signals of the prediction stage, lookup table (LUT) and subtraction stage can be fed to a device which calculates therefrom a value determining the reproduction quality of clinically relevant objects.

It has been found advantageous for the second device to have means of taking the local variance of the noise from a background image and/or means of taking the local variance of the noise from a current image of continuous current images, the second device according to the invention possibly having an addition stage which takes the sum of the variances of the two means.

Advantageously the first device can have either a Hough transformation device to which the output signals of the prediction stage, lookup table (LUT) and subtraction stage are fed, or a device for taking the variance, to which the output signals of the prediction stage, lookup table (LUT) and subtraction stage are fed.

The x-ray radiator can be provided with a multi-leaf diaphragm with collimator and/or pre-filtering unit.

The x-ray detector can be assigned an anti-scatter grid.

The clinically relevant objects can be e.g. guide wires, catheters and/or stents.

For a measuring method for checking an x-ray diagnostic apparatus, the object is achieved according to the invention by the following steps:

acquiring fluoroscopic series of x-ray images of a technical phantom (8) and storing the digital data, taking the difference between a dynamic image and a background image, predicting a measuring field, determining a priori information concerning the shape of a clinically relevant object, applying the Hough transformation on the gray value image of the difference and determining therefrom the contrast of the clinically relevant object, squaring the contrast, calculating the noise variance by summing the noise variance from a homogeneous image region and the variance of the background image, taking the ratio of contrast to the noise variance dynamically averaging the squared contrast-to-noise ratio and taking the CRFP index (Clinical Relevant Fluoroscopy Performance) for x-ray equipments.

Alternatively, for a test method for checking an x-ray diagnostic apparatus, the object is achieved according to the invention by the following steps:

acquiring fluoroscopic series of x-ray images of a technical phantom (8) and storing the digital data, taking the difference between a dynamic image and a background image,
predicting a Region of Interest (ROI),
determining a priori information concerning the shape of a clinically relevant object,
taking the variance of the clinically relevant object on the gray value image of the difference,
calculating the noise variance by summing the noise variance from a homogeneous image region and the variance of the background image,
taking the ratio of variance to noise variance,
dynamically averaging the ratio of the variances and
taking the CRFP Index (Clinical Relevant Fluoroscopy Performance) for x-ray equipments.

For a measuring method for checking clinically relevant objects by means of a standardized x-ray diagnostic apparatus the object is likewise achieved according to the invention by the following steps:

acquiring fluoroscopic series of x-ray images of a clinically relevant object and storing the digital data by means of a standardized x-ray equipment.
taking the difference between a dynamic image and a background image,
predicting a measuring field,
determining a priori information concerning the shape of a clinically relevant object,
applying the Hough-Transformation on the gray value image of the difference and determining therefrom the contrast of the clinically relevant object,
squaring the contrast,
calculating the noise variance by summing the noise variance from a homogeneous image area and the variance of the background image,
taking the ratio of contrast to noise variance,
dynamically averaging the squared contrast-to-noise ratio and
taking the CRFP index (Clinical Relevant Fluoroscopy Performance) for clinically relevant objects.

Alternatively, for a measuring method for checking clinically relevant objects by means of a standardized x-ray diagnostic apparatus, the object is likewise achieved according to the invention by the following steps:

acquiring fluoroscopic series of x-ray images of a clinically relevant object and storing the digital data by means of a standardized x-ray equipment,
taking the difference between a dynamic image and a background image,
predicting a Region of Interest (ROI),
determining a priori information concerning the shape of a clinically relevant object,
taking the variance of the clinically relevant object on the gray value image of the difference,
calculating the noise variance by summing the noise variance from a homogeneous image region and the variance of the background image,
taking the ratio of variance to noise variance
dynamically averaging the ratio of the variances and
taking the CRFP index (Clinical Relevant Fluoroscopy Performance) for clinically relevant objects.

These methods enable the visibility of guide wires and stents in x-ray images to be quantified under standardized recording conditions, thereby making possible image-quality certification of guide wires and stents in order to ensure a particular minimum quality in terms of visibility.

BRIEF DESCRIPTION OF THE DRAWINGS

The invention will now be explained in greater detail with reference to exemplary embodiments illustrated in the accompanying drawings in which.

DETAILED DESCRIPTION OF INVENTION

Figure 1:
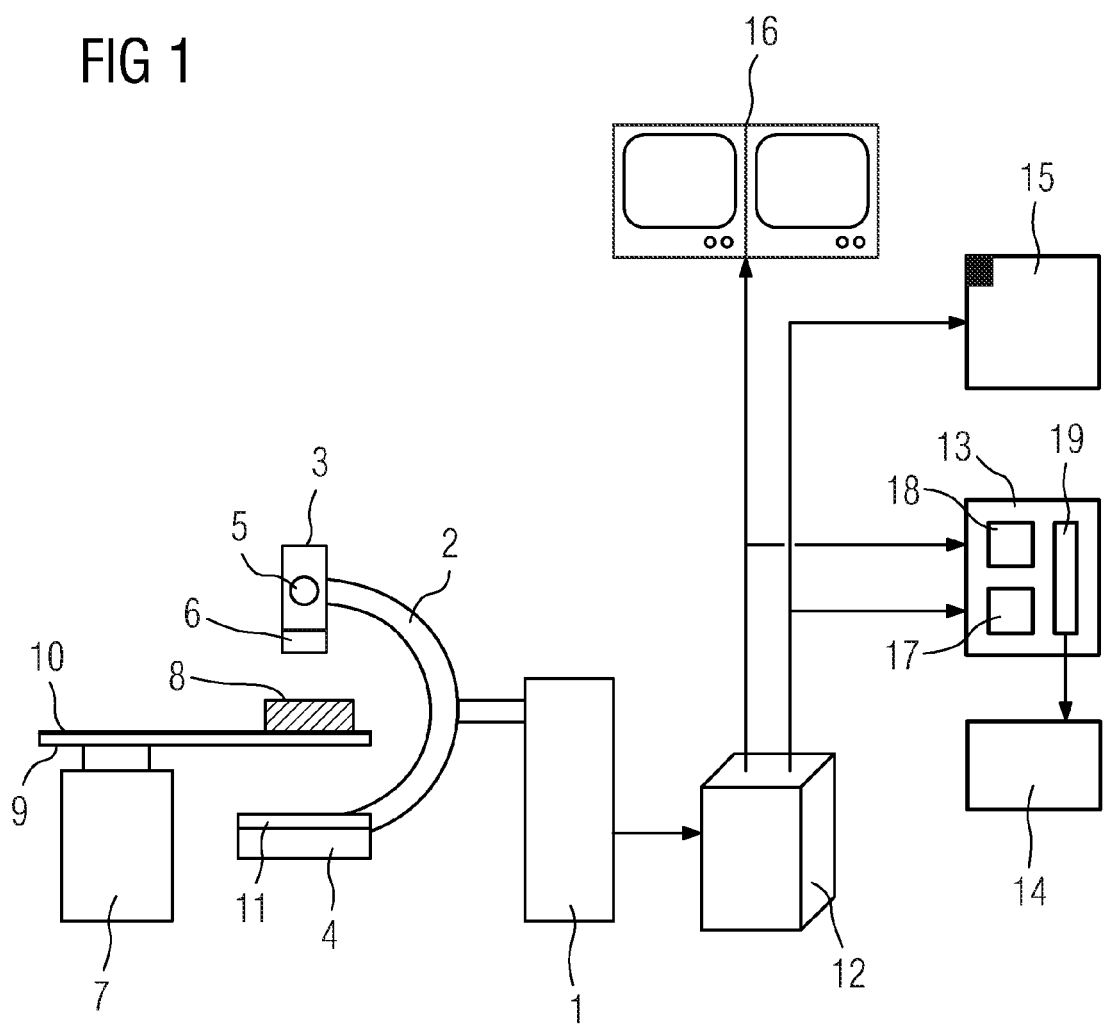
FIG. 1 shows an x-ray diagnostic apparatus according to the invention.

FIG. 1 shows an x-ray diagnostic apparatus having a C-arm 2 which is pivotally mounted on a support 1 and at whose ends there are mounted an x-ray radiator 3 and an x-ray detector 4.

Instead of the support 1 shown, floor and/or ceiling supports can also be used. The C-arm 2 may also be replaced by a so-called electronic C-arm in which the x-ray radiator and x-ray detector are electronically linked. The x-ray radiator contains an x-ray tube 5 and is provided with a multi-leaf diaphragm 6 having a collimator and a pre-filtering unit.

For test and measurement purposes there is disposed on the patient positioning table 7 a technical phantom 8 which is irradiated by the x-ray radiator 3 so that an attenuated signal corresponding to the radiation transparency of the phantom 8 is incident on the x-ray detector 4. The patient positioning table 7 generally has a positioning plate 9 and a mattress 10.

Preceding the x-ray detector 4 there is disposed an anti-scatter grid 10 which provides a known means of preventing radiation scattered by the object under examination, in this case the phantom 8, from being incident on the x-ray detector 4.

The output signal of the x-ray detector 4 is fed by the x-ray diagnostic apparatus to an imaging system 12 which is responsible for controlling the x-ray diagnostic apparatus and for the further processing of the digital image signals. In the case of determining, according to the invention, a value determining the quality of the x-ray diagnostic apparatus, the digital image signals processed in this way are fed via a receiver board 13 to a measuring device 14 which will be described in more detail below.

In the case of an x-ray examination, for example, the digital image signals can be routed via a network and/or stored in an archive 50. From the digital image signals, the imaging system 12 generates video signals in a known manner which can be reproduced on viewing monitors 16.

The receiver board 13 has a DICOM interface 17 to which the digital image signals can be fed in the DICOM standard. Alternatively, the receiver board 13 can also be fed the video signals which are digitized by means of a frame grabber 18 and converted by the software module 19 for measured value acquisition by the measuring device 14.

For the inventive gauging of the x-ray diagnostic apparatus a clinically relevant phantom with the following characteristics is used.

It has a static background of anatomical structures, such as a thorax, and/or technical structures.

It has a dynamic (moving) foreground containing the clinically relevant structures to be measured, such as guide wires and/or stents.

A standardized version of the phantom for comparing different x-ray systems with one another is present.

Figure 2:
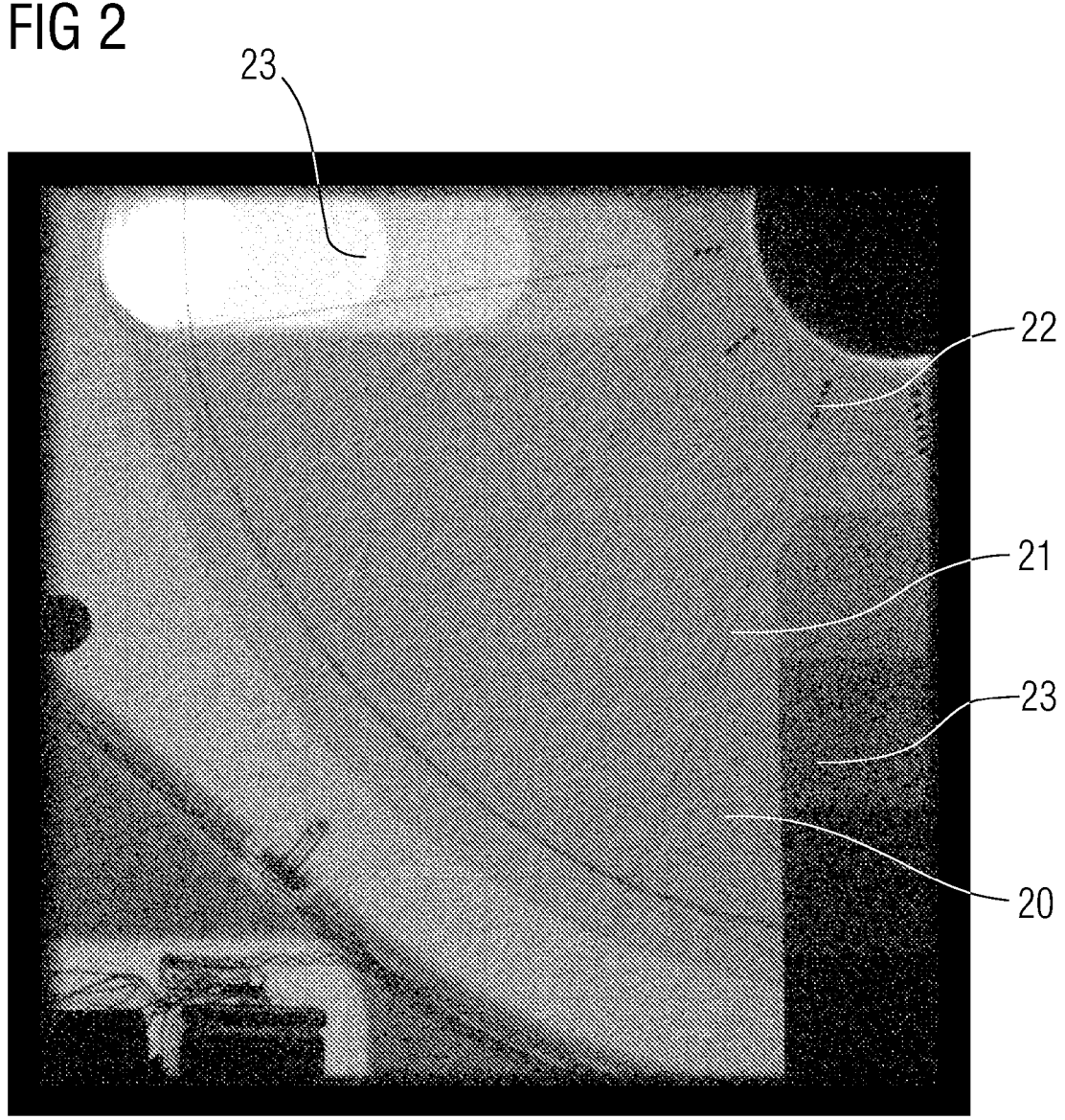
FIG. 2 shows an x-ray image of the test phantom.

FIG. 2 shows an x-ray image of a technical phantom 8 of this kind which can be used in the x-ray diagnostic apparatus for the inventive determination of the value determining the quality of the x-ray diagnostic apparatus. The phantom 8 has a rotating disk 20 in which the guide wires 21 are incorporated. In continuation of the guide wires 21, markers 22 are inserted which have a higher detectability and can be used as aids for automatic detection of the guide wires 21. The background 23 can be formed e.g. by plexiglass inserts having a patient-like scattered radiation behavior, copper step wedges and contrast plateaus.

Figure 3:
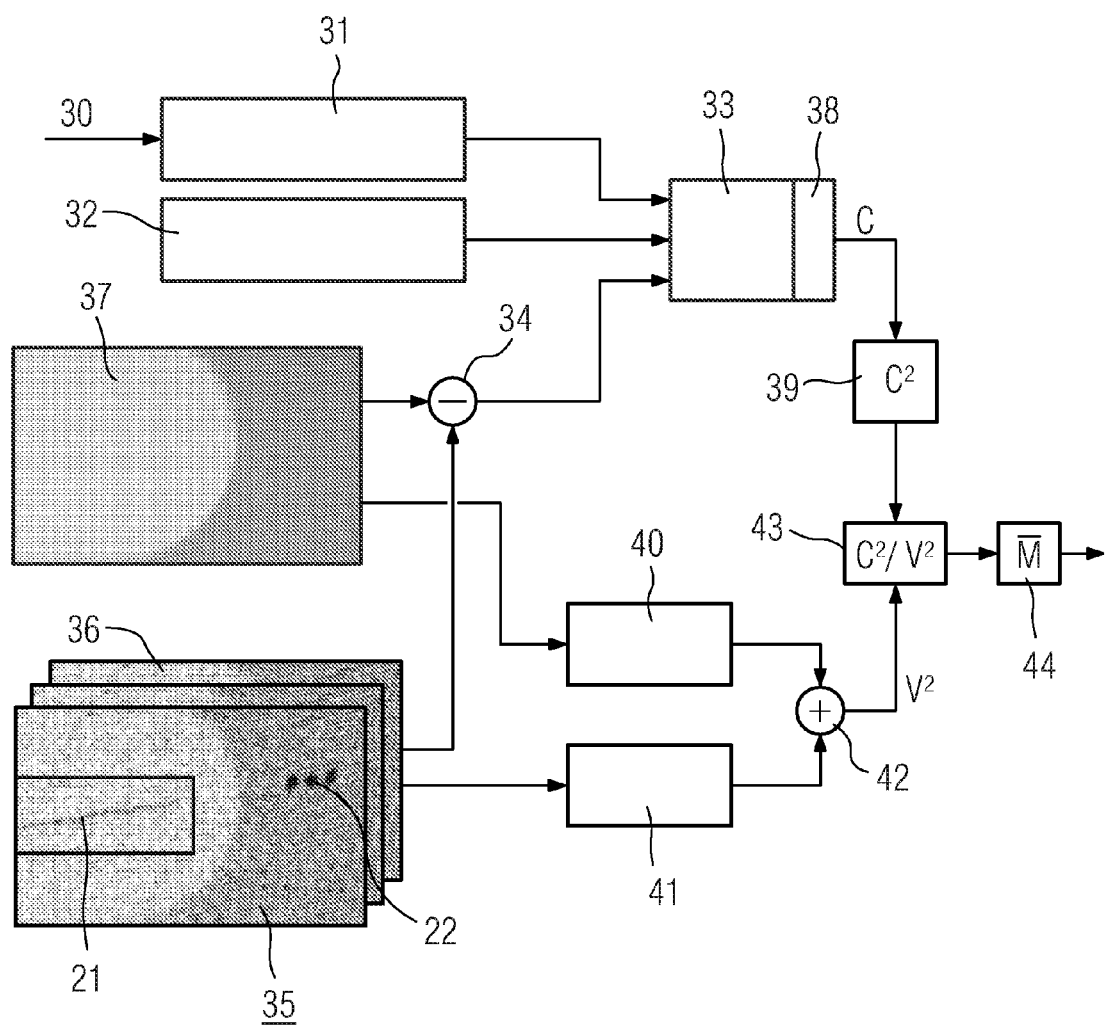
FIG. 3 shows a first embodiment of the device for determining a quality measured value according to FIG. 1

FIG. 3 describes a first embodiment of the x-ray diagnostic apparatus according to the invention, for which a quality value is obtained from the x-ray image of a guide wire 21 contained in the phantom 8. The x-ray diagnostic apparatus delivers a transducer signal 30 corresponding to the SID angulation (Source to Image Distance). From the transducer signal 30, a prediction stage 31 makes a prediction of the position of the guide wire 21. A lookup table (LUT) 32 contains the a priori knowledge concerning the shape of the guide wires 21 in the projection plane. This knowledge is retrieved and fed, together with the output signal of the prediction stage 31, to a device 33 for performing the Hough transformation known e.g. from U.S. Pat. No. 3,069,654. The shape of the guide wires 21 can be linear or square, thereby producing a straight line or a parabola.

In a subtraction stage 34, a background image 37 is extracted from a current image 36 extracted from a series of continuous images 35, the output signal of the subtraction stage 54 being available to a third input of the device 33 for performing the Hough transformation. When the Hough transformation has been performed, a contrast calculation takes place in a contrast stage 38 which detects the negative peak characterizing the guide wires 21 in the x-ray image e.g. from the noise of the Hough transformation signal and takes the difference between the peak and the mean value of the ambient noise so that it obtains a signal corresponding to the contrast C of the guide wires 21. This output signal of the contrast stage 38 is fed to a squaring stage 39.

The digital image signals of the background image 37 are additionally fed to a device 40 for taking the local variance from the noise of the background image 37, the so-called background noise, and the digital image signals of the relevant current image 36 of the continuous images 35 are fed to a device 41 for taking the local variance from the noise of a homogenous image region of the current image 36. The output signals of the two devices 40 and 41, the variances $V^2$, are summed in an addition stage 42. A following division stage 43 divides the square of the contrast $C^2$ by the variances $V^2$. From the output signal of the division stage 43, there is formed in an averaging stage 44 the dynamic mean which constitutes a so-called CRFP index (Clinical Relevant Fluoroscopy Performance Index) for guide wires as a quality value.

Figure 4:
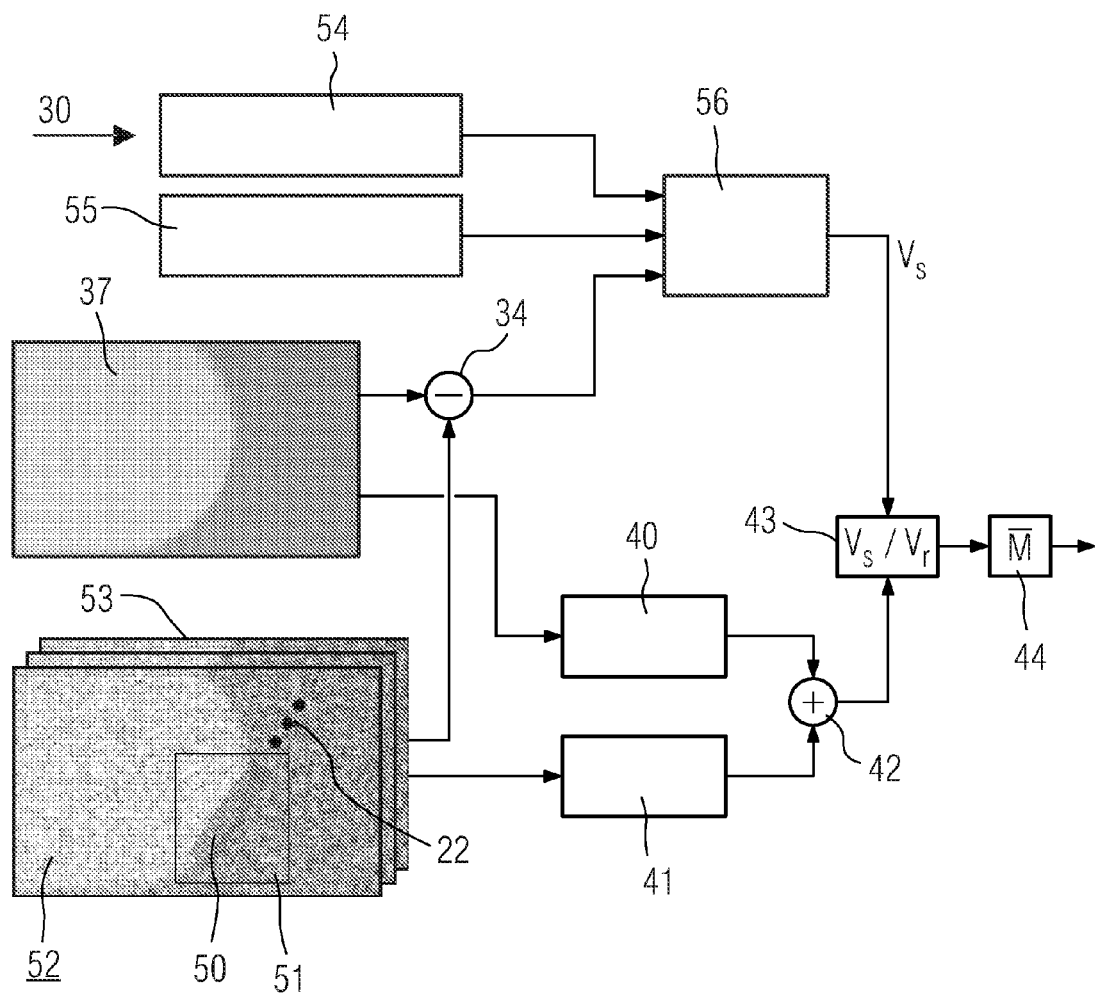
FIG. 4 Shows another embodiment of the system for determining a quality measured value according to FIG. 1.

FIG. 4 describes a second embodiment of the x-ray diagnostic apparatus according to the invention, in which a quality value is formed from the x-ray image of a stent 50 contained in the phantom 8. The stents 50 are located within a Region of Interest (ROI) 51 in continuous x-ray images 52 in which markers 22 are again disposed for better detection. The last of the continuous x-ray images 52 is the current x-ray image 53.

From the transducer signal 30 of the SID angulation, a prediction stage 54 makes a prediction of the position of the stent 50. A lookup table (LUT) 55 contains a priori knowledge about the shape of the stents 50 in the projection plane. This knowledge is retrieved and fed together with the output signal of the prediction stage 54 to a device 56 for taking the variance. The shape of the stents 50 can be linear or square, thereby producing straight lines or parabolas.

In the subtraction stage 34, the background image 37 is subtracted from a current x-ray image 53 taken from a series of continuous x-ray images 52, the output signal of the subtraction stage 34 being available to a third input of the device 56 for taking the variance $V_s$.

The digital image signals of the background image 37 are additionally fed to the device 40 for taking the local variance from the noise of the background image 37 and the digital image signals of the current image 53 of the continuous images 52 are fed to the device 41 for taking the local variance from the noise of a homogenous image region of the current image 53. The output signals of the two devices 40 and 41, the variances $V_r$, are summed in an addition stage 42. A following division stage 43 divides the variance $V_s$ by the variances $V_r$. From the output signal of the division stage 43 there is formed, in an averaging stage 44, the dynamic mean which constitutes a so-called CRFP index for stents.

Through the use of the technical phantom 8 in the x-ray diagnostic apparatus implemented according to the invention, on the one hand a highly precise measuring procedure can be carried out and, on the other, the phantom 8 contains clinically relevant objects such as guide wires and stents seen by the examiner in application to the patient. The x-ray diagnostic apparatus is operated in the manner designed for routine interventional work on the patient. The measuring method supplies an image quality value which correlates to the visual detectability of the guide wires and stents by an x-ray diagnostic apparatus.

This enables an x-ray diagnostic apparatus to be assigned a measurable Performance Index which expresses how well the x-ray equipment displays clinically relevant objects in interventional fluoroscopy to the examiner.

By means of the phantom 8, which possesses the above-mentioned clinically relevant fluoroscopic characteristics such as objects (stents & guide wires) and dynamic behavior, the comparison values of x-ray equipments are measurable.

The high-precision measuring method for determining the clinically relevant image quality of the x-ray diagnostic apparatus takes particular account of guide wires which are at the threshold of visibility.

By means of the implementation according to the invention, an interventional x-ray diagnostic apparatus with the capability of acquiring fluoroscopic images can be assigned, on the basis of settings for routine clinical operation, a measurable Performance Index which expresses how well the equipment displays clinically relevant objects in interventional fluoroscopy to the examiner. The x-ray diagnostic apparatus and its configuration explicitly comprises: radiation generation in the x-ray tube 5 (kV, mAs, dose), collimator, pre-filtering, effect of the positioning plate 9 and mattress 10, effect of the anti-scatter grid 11, effect of the x-ray detector 4, effect of the imaging system 12 and its image processing.

Fluoroscopic series can be acquired by storing the digital data or digitizing the analog video signal displayed on the viewing monitors 16 by means of so-called frame grabbers for metrological analysis. The x-ray detector 4 can be a flat panel detector or an x-ray image amplifier/TV system with analog TV camera or CCD camera.

In addition, the x-ray diagnostic apparatus according to the invention has a phantom 8 which shows clinically relevant behavior by using cardiological guide wires and stents as well as simulation of the required dynamic behavior. This can be achieved e.g. by a rotating phantom as described in connection with FIG. 2.

Moreover, the x-ray diagnostic apparatus is provided with a precision measuring method for guide wires, a measurement PC with measurement software, which takes the difference between the dynamic image and the background image. Using a predicted measuring field as well as a priori information about the shape of the guide wires, the Hough transformation is applied on the gray value image of the difference and the contrast of the guide wire is determined therefrom. The contrast is squared and set in relation to the noise variance. The noise variance consists of the sum of the noise variance from a homogenous image region and the variance of the background image. The squared contrast-to-noise ratio is dynamically averaged, thereby producing the final CRFP index (Clinical Relevant Fluoroscopy Performance) determining the quality of an x-ray diagnostic apparatus for guide wires.

In a precision measuring method according to the invention for stents, the difference is again taken between the dynamic image and the background image. The variance in the predicted ROI is then taken using a predicted measuring field as well as a priori information concerning the shape of the stent. This variance is set in relation to the noise variance. The noise variance consists of the sum of the noise variance from a homogenous image region and the variance of the background image. The ratio of the variances is dynamically averaged, thereby producing the dynamic CRFP index for stents.

Using the x-ray diagnostic apparatus according to the invention, a method of image quality assurance for angiographic x-ray diagnostic apparatuses can be carried out which enables an examiner, for example, to compare different x-ray diagnostic apparatuses, thereby ensuring that x-ray diagnostic apparatuses have a minimum image quality requirement.

In addition, by acquiring x-ray images by means of a standardized x-ray diagnostic apparatus, cardiological items such as guide wires and stents can be assigned a measurable Performance Index which expresses the visibility of the items in interventional fluoroscopy. The measuring method provides an image quality value, the clinically relevant image quality, which correlates with the visual detectability of the guide wires and stents which are at the threshold of visibility. For this purpose the cardiological items are examined and gauged according to the inventive method in a standardized x-ray diagnostic apparatus. The CRFP index can then be assigned to these cardiological items and their visibility and detectability in the x-ray image can be specified so that the physician, when purchasing them, already knows through the CRFP index whether they will still be visible in his equipment, or whether he should take cardiological items with a better CRFP index.

The invention claimed is:

1. A measuring method for checking an x-ray diagnostic apparatus, the method comprising:
   digitally acquiring fluoroscopic series of x-ray images of a technical phantom and storing the acquired digital data;
   calculating a difference between a dynamic image and a background image;
   predicting a measuring field;
   determining a-priori information about the shape of a clinically relevant object;
   applying a Hough transformation on a gray value image corresponding to the difference;
   determining a contrast of the clinically relevant object from the Hough-transformed gray value image;
   calculating a square of the determined contrast;
   calculating a noise variance by determining a sum of a noise variance of a homogenous image region and a variance of the background image;
   determining a contrast-to-noise ratio of the determined contrast and the calculated noise variance;
   dynamically averaging a square of the contrast-to-noise ratio; and
   determining a Clinical Relevant Fluoroscopy Performance (CRFP) index for the x-ray diagnostic apparatus.

* * * * *